United States Patent
Kurosawa et al.

(12)

(10) Patent No.: US 6,703,027 B2
(45) Date of Patent: *Mar. 9, 2004

(54) COMPOSITION FOR EXTERNAL USE

(75) Inventors: Mari Kurosawa, Yokohama (JP); Hiroshi Fukui, Yokohama (JP)

(73) Assignee: Shiseido Company, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,522

(22) PCT Filed: Apr. 30, 1999

(86) PCT No.: PCT/JP99/02338
§ 371 (c)(1),
(2), (4) Date: Dec. 28, 1999

(87) PCT Pub. No.: WO99/56702
PCT Pub. Date: Nov. 11, 1999

(65) Prior Publication Data
US 2002/0022037 A1 Feb. 21, 2002

(30) Foreign Application Priority Data
Apr. 30, 1998 (JP) .......................... 10-135954

(51) Int. Cl.⁷ ..................... A61K 7/02; A61K 7/035
(52) U.S. Cl. .............. 424/401; 424/400; 424/70.12; 424/70.13; 424/70.121
(58) Field of Search ................. 424/400, 401, 424/70.12, 70.13, 70.121

(56) References Cited

U.S. PATENT DOCUMENTS

| 4,980,167 | A | * | 12/1990 | Harashima et al. | ......... 424/401 |
| 5,538,793 | A | * | 7/1996 | Inokuchi et al. | ............ 428/407 |
| 5,747,049 | A | * | 5/1998 | Tominaga | ................... 424/401 |
| 6,086,903 | A | * | 7/2000 | Trinh et al. | ................. 424/401 |
| 6,117,830 | A | * | 9/2000 | Yokosuka et al. | .......... 510/242 |

FOREIGN PATENT DOCUMENTS

| JP | B-4-17162 | 3/1992 |
| JP | 07089834 | 4/1995 |
| JP | A-7-196815 | 8/1995 |
| JP | 8-134103 | 5/1996 |
| JP | 8-208989 | 8/1996 |
| JP | 10-29910 | 2/1998 |
| JP | 10-29915 | 2/1998 |
| JP | 10-29921 | 2/1998 |
| JP | A-11-60445 | 3/1999 |
| JP | 0-918-069 | 5/1999 |

OTHER PUBLICATIONS

JP 06107518 Abstract, 1994.*
JP 10029910 Abstract, Feb. 1998.*
JP 10–029910 computer generted translation.. 2000.*
RN 7631–89–9, ACS Registry Copyright 2003.*
JP 07–089834, Apr. 4, 1995, Computer generated translation.*

* cited by examiner

Primary Examiner—Russell Travers
Assistant Examiner—Shahnam Sharareh
(74) Attorney, Agent, or Firm—Foley & Lardner

(57) ABSTRACT

An external composition containing a silicone-modified polysaccharide compound and a low viscosity silicone oil and/or powder component, which is useful for covering rough surfaces on a skin.

18 Claims, No Drawings

COMPOSITION FOR EXTERNAL USE

This application is a 371 of PCT/JP99/02338 filed on Apr. 30, 1999 which claims priority to Japanese Application 10-135954 Apr. 30, 1998.

TECHNICAL FIELD

The present invention relates to an external composition, more specifically it relates to an external composition capable of covering and smoothing roughness on a skin due to various reasons, whereby it appear visually as if there were no roughness.

BACKGROUND ART

One of the most important roles for makeup cosmetics is needless to say "beautification" or making the appearance more beautiful. Specifically, this "beautification" is normally achieved by smoothing roughness caused by small pores in the skin and correcting the color of the skin.

However, it is true that there is quite a bit of skin roughness which is difficult to correct even using conventional makeup cosmetics.

For example, (1) skin roughness which has become noticeable to an extent forming "craters" due to acne etc. and (2) keratoids due to burns or skin grafts, (3) surgical scars, (4) deep wrinkles, (5) deep scars, (6) large pores or small wrinkles, etc. are difficult to correct by makeup cosmetics.

That is, among makeup cosmetics, oily solid cosmetics containing powder components, oil components, and wax and emulsified solid cosmetics containing powder components, oil components, wax, water, and a humectant bury the roughness, etc. caused by small pores in the skin by the wax contained therein, but these are flexed by the movement of the skin and sometimes end up falling off so cannot correct large roughness of the skin such as in the above (1) to (5). Further, in conventional makeup cosmetics, since the refractive indexes of the components differ, the color applied becomes opaque and, as a result, pitting becomes opaque at the time of coating and bumps become highly transparent. Even if the roughness is flattened, the pitting ends up visually standing out, and therefore, the result is not practical.

Further, when trying to forcibly correct the large pores and small wrinkles of the above (6) by existing makeup cosmetics, there has been a strong tendency for an unnatural finish to result.

Therefore, there has been a desire to provide an external composition capable of smoothing large and small roughness on the skin, including roughness which had been difficult to correct by conventional makeup cosmetics as described above, and make the roughness no longer stand out visually.

When large roughness on the skin such as the above (1) to (5) is corrected, the external composition to be provided must adhere to the skin, without falling off etc. even when coated thickly on the skin, not run due to gravity, and be able to be easily removed from the skin. Further, preferably it should be high in transparency and be able to correct roughness to appear as if there were no pitting or bumps on the skin.

Further, when correcting the large pores and small wrinkles of the above (6), it is necessary that the composition adhere to the skin, without falling off etc. even if thickly coated on the skin and enable correction so that it appears if there are no pores or small wrinkles while maintaining a natural feeling and also retain this corrective effect over a long period of time (at least 2 hours or more).

The present inventors have already provided, as a means for solving part of this problem, a roughness correcting composition having these desired characteristics by formulating a high viscosity silicone oil having both suitable adhesion to and peelability from the skin and, to correct running on the skin due to the nature of this silicone oil as a Newtonian fluid, a powder component (see Japanese Patent Application No. 9-227603).

This roughness correcting composition solved part of the main problem above in that it adhered to the skin, without falling off even when coated thickly on the skin and did not run due to gravity and, at the same time, could be easily removed from the skin, was high in transparency, and enabled correction of roughness to make it seem if it were not there. When a long time passed from when it was coated on the skin, however, the portions entering into deeper portions of the skin ended up appearing white and broke up by movement of the skin after coating, and therefore, the last with the elapse of time (the adhesion of this composition) and toughness were not sufficient.

DISCLOSURE OF INVENTION

Accordingly, the object of the present invention is to provide an external composition superior in last (the adhesion of this composition) and toughness and capable of correcting of skin roughness etc.

In accordance with the present invention, there is provided an external composition containing a silicone-modified polysaccharide compound and a low viscosity silicone oil and/or powder component.

BEST MODE FOR CARRYING OUT THE INVENTION

That is, the present inventors engaged in intensive studies to solve the above problem and, as a result, found that it is possible to obtain a desired external composition (hereinafter also referred to as the external composition of the present invention) by formulating a silicone-modified polysaccharide compound such as silicone-modified pullulan into the external composition as a component for correcting the skin roughness.

The external composition of the present invention contains a low viscosity silicone oil and/or powder component. As the powder component, inclusion of at least a powder component having a refractive index of 1.3 to 1.5 such as silicon dioxide powder, silicone resin powder, silicone rubber powder, and silicone resin coated rubber powder is preferable.

Further, in the external composition of the present invention, as explained below, the hardnesses or shapes etc. of the powder particles of the powder component formulated are suitably selected to be able to impart various properties.

Further, in the external composition of the present invention, as explained below, a volatile component such as volatile silicone or water is formulated so as to set the thickness of coating of the composition on the skin to a specific thickness for use in various modes.

The external composition of the present invention may be roughly divided into two types of aspects of external compositions.

One external composition of the present invention is an external composition for correcting large roughness on the skin such as the above (1) to (5) and specifically is an external composition expressed mainly as a "roughness correcting composition" (the external composition of this aspect of the present invention sometimes also being called the roughness correcting composition of the present invention).

In the external composition of the present invention, the contents of the silicone-modified polysaccharide compound and the low viscosity silicone oil are preferably in total at least 70.0% by weight of the weight of the external composition as a whole minus the weight of the powder component (in the case where a volatile component is included in the external composition, the weight of the powder component and the volatile component). Further, at least 90.0% by weight of the powder component formulated as a whole is preferably a powder component having a refractive index of 1.3 to 1.5.

The other external composition of the present invention is an aspect of an external composition used as a general makeup cosmetic composition, but is a "makeup composition" capable of covering large pores or small wrinkles (above (6)), which had been difficult to naturally cover in the past, while maintaining a natural look (the external composition of this aspect of the present invention also being called the makeup composition of the present invention).

In the makeup composition of the present invention, the total content of the silicone-modified polysaccharide compound and the low viscosity silicone oil in the external composition is preferably at least 60.0% by weight of the weight of the external composition as a whole minus the weights of the powder component and the volatile component. Further, at least 20.0% by weight of the powder component formulated as a whole is preferably a powder component having a refractive index of 1.3 to 1.5.

The embodiments of the present invention will be explained in detail below:

A. Formulation Components in External Composition of Present Invention (1) Silicone-modified Polysaccharide Compound The external composition of the present invention is an external composition containing a silicone-modified polysaccharide composition as a component for correcting skin roughness.

As explained above, the external composition of the present invention is roughly divided into two aspects of a "roughness correcting composition" and a "makeup composition", but in both aspects, a silicone-modified polysaccharide composition is formulated as the component for correcting the skin roughness ("skin roughness" meaning roughness on the skin in general unless otherwise indicated. That is, (1) skin roughness which has become noticeable to an extent forming "craters" due to acne etc., (2) keratoids due to burns or skin grafts, (3) surgical scars, (4) deep wrinkles, (5) deep scars, (6) large pores and small wrinkles etc. (mentioned above) capable of being effectively corrected by the external composition of the present invention, of course, and also skin roughness capable of being covered by existing makeup cosmetics, for example, small pores etc. correspond to "skin roughness".)

This silicone-modified polysaccharide compound is described in Japanese Unexamined Patent Publication (Kokai) No. 10-29910. Specifically, it is a compound having the following formula (I):

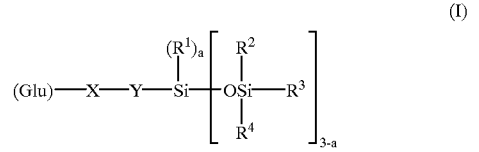

(I)

wherein Glc is a sugar residue of a polysaccharide compound, X is a bivalent bond group, and Y is a bivalent aliphatic group, $R^1$ is a $C_1$ to $C_8$ monovalent organic group, $R^2$, $R^3$, and $R^4$ each indicate a $C_1$ to $C_8$ monovalent organic group or siloxy group of $-OSiR^5R^6R^7$ where $R^5$, $R^6$, and $R^7$ are each $C_1$ to $C_8$ monovalent organic groups. Further, a is 0, 1, or 2.

In the formula (I), Glc represents a sugar residue of a polysaccharide compound. As the polysaccharide compound, various known polysaccharide compounds, for example, cellulose, hemicellulose, gum arabic, tragacanth gum, tamarind gum, pectin, starch, mannan, guar gum, locust bean gum, quince seed gum, alginic acid, carrageenan, agar, xanthane gum, dextran, pullulan, chitin, chitosan, hyaluronic acid, chondroitin sulfuric acid, etc., derivatives of polysaccharide compounds, for example, carboxymethylated derivatives, sulfate derivatives, phosphated derivatives, methylated derivatives, ethylated derivatives, addition derivatives of alkylene oxide such as ethylene oxide or propylene oxide, acylated derivatives, cationated derivatives, low molecular weight derivatives, and other polysaccharide derivatives may be mentioned. Among these polysaccharide compounds, it is preferable to select ethyl cellulose or pullulan as polysaccharide compounds. In particular, it is preferable to select pullulan. Further, the molecular weight of the polysaccharide compound differs by the type of the polysaccharide, but it is preferably about 1,000 to 5,000,000.

These polysaccharides, depending upon the type, contain one or more types of reactive functional groups such as a hydroxyl group or carboxyl group. The bivalent bonding group shown by X is an A-derived bivalent bond group formed by the reaction between a reactive functional group contained by this polysaccharide compound and a silicone compound having the following general formula (II):

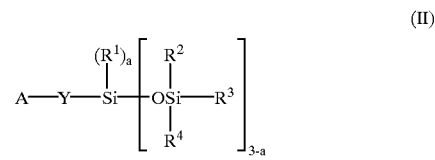

(II)

wherein Y, $R^1$, $R^2$, $R^3$, $R^4$, and a are the same as defined in the formula (I). Further, A is a functional group capable of reacting with the reactive functional group of the polysaccharide compound, for example, an isocyanate group, epoxy group, vinyl group, acryloyl group, methacryloyl group, amino group, imino group, hydroxyl group, carboxyl group, mercapto group, etc. Note that it is possible to use a conventionally known method for the reaction with the polysaccharide compound and silicone compound.

As the bivalent bond group X formed in this way, for example, a carbamoyl group, $-CH_2CH(OH)-$, carbonyl group, amino group, ether group, etc. may be mentioned, but from the standpoint of reactivity a carbamoyl group ($-CONH-$) formed by the reaction of a compound having the formula (II) where A is an isocyanate group ($O=C=N-$) and the reactive functional group of the polysaccharide compound, that is, the hydroxyl group is preferable. Note that the sugar residue Glc of the polysaccharide compound in this case indicates the remaining part of the polysaccharide compound after removing the hydrogen atom of the hydroxyl group reacting with the isocyanate group. In the case of other reactions as well, the sugar residue of the polysaccharide represents one based on this.

Y is a bivalent aliphatic group. As this bivalent aliphatic group, for example, an alkylene group, an alkylene group having in its main chain an oxygen atom, nitrogen atom, sulfur atom, etc., an alkylene group having in its main chain an arylene group such as a phenylene group, an alkylene group having in its main chain a carbonyloxy group or oxycarbonyl group, etc. may be mentioned. These bivalent aliphatic groups may have substituents such as a hydroxy group, alkoxy group, alkyl group, etc. Further, the terminal atom of the aliphatic group may be a hetero atom such as an oxygen atom, nitrogen atom, or sulfur atom. Examples of Y are —$(CH_2)_2$—, —$(CH_2)_3$—, —$(CH_2)_4$—, —$(CH_2)_6$—, —$(CH_2)_8$—, —$[CH_2CH(CH_3)]$—, —$(CH_2)_2O(CH_2)_3$, —$CH_2CH(OH)$—$CH_2$—, etc. Among these, the propylene group represented by —$(CH_2)_3$— is preferable.

$R^1$, $R^5$, $R^6$, and $R^7$ represent $C_1$ to $C_8$ monovalent organic groups. Further, $R^2$, $R^3$, and $R^4$ may represent a $C_1$ to $C_8$ monovalent organic group. As such a monovalent organic group, for example, an alkyl group such as a methyl group, ethyl group, propyl group, and butyl group; a cycloalkyl group such as a cyclopentyl group and cyclohexyl group; an aryl group such as a phenyl group; an aralkyl group such as a benzyl group; an alkenyl group such as a vinyl group and allyl group; and a fluorinated alkyl group such as a 3,3,3-trifluoropropyl group may be mentioned.

Further, $R^2$, $R^3$, and $R^4$ may each represent a siloxy group represented by —$OSiR^5R^6R^7$. As such a siloxy group, a trimethylsiloxy group, ethyldimethylsiloxy group, phenyldimethylsiloxy group, vinyldimethylsiloxy group, 3,3,3-trifluoropropyldimethylsiloxy group, etc. may be mentioned.

$R^1$, R2, R3, $R^4$, $R^5$, $R^6$, and $R^7$ may be the same or different, but $R^2$, $R^3$, and $R^4$ preferably are all methyl groups. a represents 0, 1, or 2, but a=0 is preferable.

As the silicone-modified polysaccharide compound used in the external composition of the present invention, a particularly preferred one is the silicone-modified pullulan of the following formula (III):

one produced by a usual known method of production. Further, a commercially available one may be included.

The amount of the above silicone-modified polysaccharide compound in the external composition of the present invention is suitably selected depending upon the properties of the external composition of the present invention planned. It differs depending on the type of the specific silicone-modified polysaccharide compound. While not particularly limited, it is preferably 0.1 to 40.0% by weight based upon the external composition of the present invention as a whole. If the amount of the silicone-modified polysaccharide compound is less than 0.1% by weight based upon the external composition of the present invention as a whole, even if the composition obtained is coated on the skin, a thickness necessary for burying the roughness on the skin cannot be obtained and, further, the adhesion to the skin and toughness are insufficient. If the amount is more than 40.0% by weight, it is not possible to spread the composition obtained on the skin, and therefore, this is not preferred.

(2) Low Viscosity Silicone Oil

The external composition of the present invention may include a low viscosity silicone oil in addition to the above silicone-modified polysaccharide compound.

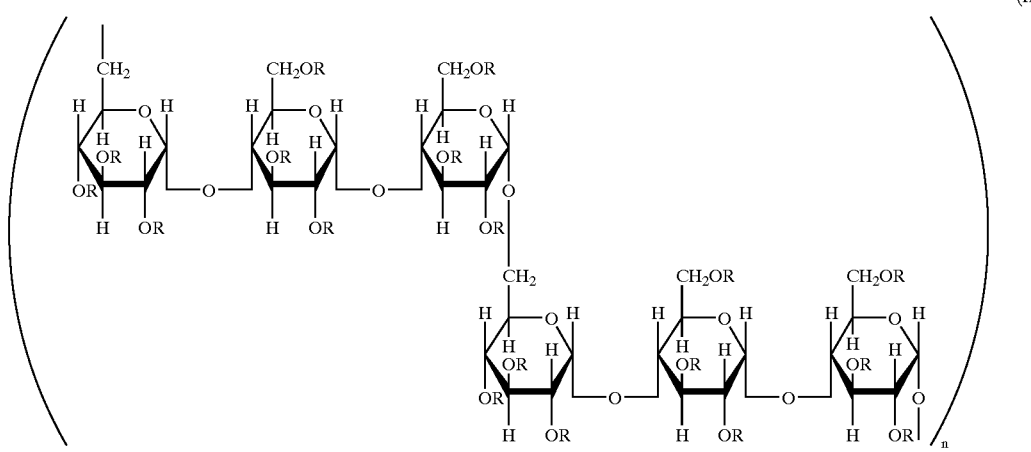

(III)

wherein R represents a hydrogen atom or $[(CH_3)_3SiO]_3Si(CH_3)_3NHCO$ group (see Japanese Unexamined Patent Publication (Kokai) No. 8-134103).

Note that the ratio of bonds in the silicone compound with respect to the reactive functional groups of the polysaccharide compound in the silicone-modified polysaccharide compound formulated into the external composition of the present invention does not necessarily have to be 100%, but if the ratio of bonds of the silicone compound with respect to the polysaccharide compound is too low, the effect of the present invention is not sufficiently manifested. The ratio of bonds differs depending on the type of the silicone compound and polysaccharide compound, but the average number of bonds (i.e., substitution degree) of the silicone compound per unit component sugar of the polysaccharide compound is preferably 0.5 to 2.5. Note that the above substitution degree is obtained by conversion from the Si content (% by weight) in the silicone-modified polysaccharide compound.

In the external composition of the present invention, the above silicone-modified polysaccharide compound may be As this low viscosity silicone oil, for example, a low molecular weight silicone oil having the formula (IV) or formula (V):

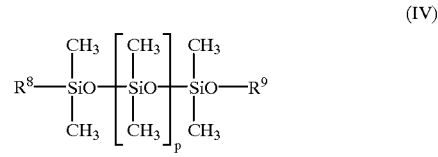

wherein $R^6$ and $R^9$ may be the same or different and represent a methyl group or hydroxy group and p is an integer of 0 to 5.

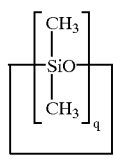

$$(\text{V})$$

wherein q is an integer of 3 to 7 for example, dimethyl polysiloxane, where $R^6$ and $R^9$ are methyl groups, may be mentioned.

As this silicone oil, further, organo polysiloxanes such as methyl hydrogen polysiloxane, methylphenyl polysiloxane, methyl polycyclosiloxane, alkyl-modified silicone, amine-modified silicone, epoxy-modified silicone, carboxyl-modified silicone, chloroalkyl-modified silicone, alkyl higher alcohol ester modified silicone, alcohol-modified silicone, polyether modified silicone, fluoro-modified silicone may be mentioned.

Among these silicone oils, dimethyl polysiloxane, methyl hydrogen polysiloxane, or methylphenyl polysiloxane are preferably selected and formulated into the external composition of the present invention when considering the safety of the external composition of the present invention on the skin, the transparency of the external composition of the present invention when formulated, and the ease of acquisition at the present point of time.

As the above low viscosity silicone oil, preferably a silicone oil having a viscosity of 1 mPa·s to 1000 mpa·s at 25° C., particularly preferably 1 mPa·s to 100 mPa·s, may be selected and added.

As the low viscosity silicone oil capable of formulating in the external composition of the present invention, it is possible to use those produced by a usual known method of production. Further, it is also possible to use a commercially available silicone oils.

The mode of formulation of the low viscosity silicone oil in the external composition of the present invention differs depending on if the external composition of the present invention is a "roughness correcting composition" or a "makeup composition", so will be explained later.

(3) Powder Component

The external composition of the present invention preferably includes, in addition to the above silicone-compound, one or more powder components.

The powder component which may be included in the external composition of the present invention is not particularly limited. Powder components based on inorganic components such as talc, kaolin, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal salts of tungstenic acid, magnesium, silica, zeolite, barium sulfate, sintered calcium sulfate (sintered gypsum), calcium phosphate, fluorapatite, hydroxyapatite, ceramic powder, metal soap (zinc myristate, calcium palmitate, ammonium stearate), boronitride, etc.; and organic powder components such as polyamide resin powder (nylon powder), polyethylene powder, polymethyl methacrylate powder, polystyrene powder, copolymer resin powder of styrene and acrylic acid, benzoguanamine resin powder, silicone resin powder, silicone rubber powder, silicone resin covered rubber powder, polyethylene tetrafluoride powder, cellulose powder, etc. may be mentioned.

Further, powder components obtained by treating the surfaces of these powder components by a silicone compound, fluorine-modified silicone compound, fluorine compound, higher aliphatic acid, higher alcohol, aliphatic acid ester, metal soap, amino acid, alkyl phosphate, etc. may be formulated into the external composition of the present invention depending upon the need.

Part or all of these powder components are preferably formulated into the external composition of the present invention as powder components having a refractive index (in the present invention, which means the refractive index calculated according to the Snell's law) having about 1.3 to 1.5. That is, this range of refractive index substantially overlaps the refractive index of the other components, that is, the silicone-modified polysaccharide compound and the low viscosity silicone oil. By combining these and adding the power components having this range of refractive index and formulating them into the external composition of the present invention, an external composition of the present invention not impairing the transparency of the silicone-modified polysaccharide compound and the low viscosity silicone oil in the desired range is provided.

Specifically, as the powder component having this range of refractive index, for example, silicon dioxide powder, silicone resin powder, silicone rubber powder, silicone-resin coated rubber powder, etc. may be mentioned.

The silicon dioxide powder is commercially available as so-called silica powder (for example, Kemiseren (made by Sumitomo Chemical), spherical silica P-1500 (Shokubai Kasei Kogyo), Aerogil #200 (Degussa), Aerogil R972, Sildex L-51 (made by Asahi Glass), etc.) In the external composition of the present invention, it is possible to use these commercially available products. By formulating these silicon dioxide powders into the external composition of the present invention, it is possible to improve the adhesive force of the external composition of the present invention on the skin.

The silicone resin powder is obtained by powderizing a silicone resin obtained by copolymerizing polyfunctional siloxane components. Various types of silicone resin powders are commercially available. As such commercially available products, for example, the Tospearl Series (Tospearl 145A etc.) made by Toshiba Silicone may be mentioned. These silicone resin powders have refractive indexes substantially the same as the silicone-modified polysaccharide compound and low viscosity silicone oil, and therefore it is possible to maintain a system mixed therewith transparent.

The silicone rubber powder may be, for example, an organopolysiloxane powder made from an organopolysiloxane elastomer composition or organopolysiloxane resin composition, for example, a cured organopolysiloxane powder having a particle size of 100 microns or less (see Japanese Examined Patent Publication (Kokoku) No. 4-17162) etc. Various silicone rubber powders are commercially available. As such commercially available products, for example, the Torayfil series (Torayfil E506W, Torayfil E505C, Torayfil E506C, Torayfil E505W, etc.) made by Toray Dow-Corning Silicone may be mentioned. In particular, these silicone powders have a greater elasticity than other powder components. By blending these in the external composition of the present invention, it is possible to make the elasticity of the external composition of the present invention close to that of the elasticity of the skin and make the composition close to the state of true skin.

The silicone resin coated rubber powder is obtained by covering spherical fine particles of silicone rubber with a polyorganosilsesquioxane resin (Japanese Unexamined Patent Publication (Kokai) No. 7-196815). As a commercial product, for example, X-52-1139K made by Shin-Etsu Chemical etc. may be mentioned. By formulating silicone resin coated rubber powder into the external composition of the present invention, it is possible to improve the ease of spreading of the external composition of the present invention on the skin.

The specific types and combinations of the above powder components capable of formulating into the external composition of the present invention may be suitably selected depending upon the need.

For example, by selecting a rubber powder component (as typical examples of a rubber powder component, the above silicone powder and silicone resin coated rubber power able to be mentioned) having a hardness of the powder particles having an average rubber hardness (the "average rubber hardness" meaning the score of Type A (intermediate hardness test) of the Durometer Hardness Test of the method of testing the hardness of vulcanized rubber and thermoplastic rubber (JIS K6253)) of less than 50 as at least part of the powder component and formulating it in the external composition of the present invention, it is possible to impart pliability to the external composition of the present invention. If selecting as the rubber powder component only one with a hardness of the powder particles having at least an average rubber hardness of 50 and formulating it in the external composition of the present invention, the composition obtained becomes too hard and spreading on the skin becomes difficult.

Further, if a powder component having a hardness of the powder particles of less than an average rubber hardness of 50 and another powder component, specifically, a powder component having an average rubber hardness of more than 50 or an inorganic powder such as silicon dioxide, are combined and formulated in the external composition of the present invention as the powder component, an external composition of the present invention having an excellent last (the adhesion of this composition) can be obtained.

Further, the form of the particles of the powder component may be spherical, plate-like, or amorphous, but it is preferable to combine at least two types of powder components of different particle shapes, for example, a powder component with a spherical particle shape (for example, a rubber powder component) and an amorphous powder component (for example, an inorganic powder component such as silicon dioxide powder having amorphous powder particles) for formulation in the external composition of the present invention.

By combining at least two types of powder components of different particle shapes in this way, in particular, a rubber powder component with spherical powder particles and having an average rubber hardness of less than 50 and an inorganic powder component with amorphous powder particles, it is possible to improve the last (the adhesion of this composition) in the external composition of the present invention.

Note that by including a powder component having amorphous powder particles as the powder component, it is possible to improve the thixotrophy of the external composition of the present invention and improve the stability with the elapse of time of the composition. Specifically, when it is necessary to positively adjust the thickness of coating of the external composition of the present invention on the skin (in particular, corresponding to the case where the external composition of the present invention is a "makeup composition") and further improve the stability with the elapse of time of the external composition, it is possible to include a powder component having amorphous powder particles to improve the stability with the elapse of time.

Further, when including combined together a powder component having a different particle shape in the external composition of the present invention, the ratio of formulation of the powder component with spherically shaped particles, in particular, the rubber powder component with spherically shaped particles, and the powder component with other shaped particles, for example, plate shaped or amorphous particles may be suitably selected depending upon the type and object etc. of the specific external composition of the present invention. It should not be particularly limited.

That is, the majority of the powder component as a whole formulated in the external composition of the present invention may be made a powder component of powder particles of any shape (including amorphous). The powder component also may be formulated by a mutually competitive volume ratio.

For example, when formulating a powder component with amorphous particles along with a powder component of another particle shape into the external composition of the present invention, the powder component with the amorphous particle shape may in general be formulated in a ratio selected with an extremely broad range of about 10 to 90% by weight (the numeral range of the ratio of formulation being a provisional measure) of the powder component formulated as a whole.

If the amount of formulation of the powder component having the amorphous particle shape is too small relatively (in the above example, less than about 10% by weight of the powder component as a whole), in the case of (1) where the external composition of the present invention is a roughness correcting composition, the last (the adhesion of this composition) is insufficient, while in the case of (2) where the external composition of the present invention is a makeup composition, it becomes difficult to sufficiently bring out the effect of correction of large pores or small wrinkles. Conversely, if the amount of formulation of the powder component having the amorphous particle shape is too large relatively (in the above example, over about 90% by weight of the powder component as a whole), in the case of (1) where the external composition of the present invention is a roughness correcting composition, the pliability and toughness of the composition obtained are insufficient and the composition easily breaks up due to the movement of the skin at the time of coating on the skin, while in the case of (2) where the external composition of the present invention is a makeup composition, there is a strong tendency for the stability with the elapse of time of the composition to deteriorate.

In the external composition of the present invention, depending on the form, it is possible to positively add color. In such a case, it is possible to formulate in a dye or pigment into the external composition of the present invention.

As the dye or pigment, usually known ones may be used. For example, inorganic white pigments such as titanium dioxide, zinc oxide, inorganic red pigments such as iron oxide (bengala), iron titanate, inorganic brown pigments such as γ-iron oxide; inorganic yellow pigments such as yellow iron oxide, yellow earth; inorganic black pigments such as black iron oxide, carbon black, lower titanium oxide, and; inorganic violet pigments such as mango violet, cobalt violet; inorganic green pigments such as chromium oxide, chromium hydroxide, cobalt titanate; blue pigments such as prussian blue, ultramarine; pearl pigments such as titanium oxide coated mica, titanium oxide coated bismuth oxichloride, titanium oxide coated talc, colored titanium oxide coated mica, bismuth oxichloride, fish scales; metal powder pigments such as aluminum powder, copper powder; organic pigments of zirconium, barium or aluminum lakes etc. such as Lithol rubine B (Red No. 201), Lithol rubine BCA (Red No. 202), Lake red CBA (Red No. 204), Lithol red (Red No. 205), Deep maroon (Red No. 220), Helidone pink CN (Red No. 226), Permatone Red (Red No. 228), Permanent red F5R (Red No. 405), Permanent orange (Orange No. 203), Benzidine Orange (Orange No. 204), Benzidine yellow G (Yellow No. 205), Hanza Yellow (Yellow No. 401), Blue No. 404, and other organic pigments; Erythrosine (Red No. 3), Phloxine B (Red No. 104), Acid red (Red No. 106), Fast acid magenta (Red No. 227), Eosine YS (Red No. 230), Violamine R (Red No. 401), Oil red XO (Red No. 505), Orange II (Orange No. 205), Tartrazine (Yellow No. 4), Sunset yellow FCF (Yellow No.

5), Uranine (Yellow No. 202), Quinoline yellow (Yellow No. 203), Fast green FCF (Green No. 3), Brilliant blue FCF (Blue No. 1) may be mentioned.

Note that among these dies and pigments, dies and pigments which are present as powder components after formulated in the external composition of the present invention are treated as the "powder components" in the present invention.

The amount of the powder component as a whole formulated in the external composition of the present invention should be suitably set depending upon the type and specific surface area of the powder component to be added (i.e., the larger the specific surface area of the powder component added, the smaller the suitable amount of the powder component) and is not particularly limited, but is preferably 5 to 80% by weight of the composition as a whole. If the amount is less than 5% by weight of the composition as a whole, there is a strong tendency that the running of the external composition of the present invention when used on the skin cannot be sufficiently suppressed. If over 80% by weight is formulated, there is a strong tendency that maintaining the external composition of the present invention in a paste state becomes difficult.

Note that the form of the formulation of the powder component having a refractive index of about 1.3 to 1.5 in the external composition of the present invention differs depending on whether the external composition of the present invention is a "roughness correcting composition" or a "makeup composition", and therefore this will be explained below.

(4) Volatile Component

The external composition of the present invention may have formulated into it along with the above components, depending upon the need, a volatile component. As the volatile component, it is possible to select a volatile component ordinarily used in external compositions such as cosmetics. Specifically, it is possible to mention, for example, volatile silicone oil, water, or a lower alcohol (or mixtures of the same). These volatile components may be suitably selected depending upon the specific form of the external composition of the present invention (for example, the later mentioned "roughness correcting composition" or "makeup composition" etc.) or type of carrier (for example, oil base or emulsion base etc.). By formulating these volatile components, it is possible to adjust the viscosity of the product at the time of use of the external composition of the present invention and adjust the thickness of coating of the external composition on the skin.

As the volatile silicone oil, it is possible to use a volatile silicone oil which is used in the field of cosmetics and other external compositions. It is not particularly limited. Specifically, for example, a low boiling point linear silicone oil such as hexamethyl disiloxane, octamethyl trisiloxane, decamethyl cyclopentasiloxane, dodecamethyl cyclohexasiloxane, and tetradecamethyl cycloheptasiloxane; a low boiling point cyclic silicone oil such as octamethyl cyclotetrasiloxane, decamethyl cyclopentasiloxane, dodecamethyl cyclohexasiloxane, and tetradecamethyl cycloheptasiloxane; etc. may be mentioned.

As the lower alcohol, ethanol etc. may be mentioned.

The form of formulation of the volatile component in the external composition of the present invention differs depending on whether the external composition of the present invention is a "roughness correcting composition" or "makeup composition", so will be explained below.

(5) Other Formulation Components

The external composition of the present invention may contain, depending upon the need, the following other components as auxiliary components to an extent not detracting from the desired effect of the present invention.

For example, as the oil component, hydrocarbon oils such as liquid paraffin, isoliquid paraffin, squalane, oils and fats such as olive oil, palm oil, coconut oil, macadamia nut oil, jojoba oil; higher alcohols such as isostearyl alcohol; ester oils such as higher aliphatic oils and isopropyl myristate, etc. may be formulated in the external composition of the present invention. Among these oil components, in particular, formulating a polar oil in the external composition of the present invention enables improvement of the stability with the elapse of time.

Further, a benzophenon derivative, para-aminobenzoate derivative, para-methoxysuccinate derivative, salicylate derivative, and other UV absorbers; humectants, blood circulation promoters, refrigerants, antiperspirants, bactericides, skin activators, anti-inflammatory agents, vitamins, antioxidants, antioxidant adjuvants, preservatives, flavors and fragrances, etc. may be blended in the external composition of the present invention.

The external composition of the present invention may be produced as a viscous paste by mixing and kneading the above essential components and, in some cases, the above auxiliary components, using a kneader, grind will, rollers, mixer, etc.

Note that the above powder component may be mixed using a usual mixer, but preferably it is mixed using a mixer having a high shearing force if possible.

B. Specific Aspects of External Composition of Present Invention

As explained above, the external composition of the present invention includes mainly the aspects of a "roughness correcting composition" and "makeup composition". Below, typical embodiments of each will be explained.

(1) Case Where External Composition of Present Invention is "Roughness Correcting Composition"

The "roughness correcting composition" means an external composition having as its main object the positive correction of relatively large skin roughness such as (1) skin roughness which has become noticeable to an extent forming "craters" due to acne etc. and (2) keratoids due to burns or skin grafts, (3) surgical scars, (4) deep wrinkles, and (5) deep scars.

To effectively achieve this object, the property capable of being coated relatively thickly on the skin (coating layer having a thickness of about 1 to 3 mm), superior transparency, and other properties are normally sought.

To enable this thick coating and transparency to be maintained suitably, it is possible to add the following elements in the roughness correcting composition of the present invention.

That is, the amount of formulation of the low viscosity silicone oil in the external composition of the present invention is not particularly limited, but when the external composition of the present invention is a roughness correcting composition, by formulating the low viscosity silicone oil so as to give a range of viscosity, together with the silicone-modified polysaccharide composition, of 1 mPa·s to 15,000,000 mPa·s, preferably 1 mPa·s to 1,000,000 mPa, particularly preferably 1 mPa·s to 100,000 mPa·s, at 25° C., it is possible to coat the external composition of the present invention thickly on the skin and possible to improve the adhesion on the skin and the ease of spreading on the skin. Note that in the present invention, when referring to "viscosity", unless otherwise indicated, it means the viscosity obtained when measuring the viscosity by a Shibaura Vismetron available from Shibaura System K.K. with a rotor no. 7 at a speed of 0.5 rpm (measured in a 25° C. constant temperature chamber).

In this case, the amount of combined formulation of the silicone-modified polysaccharide composition and the silicone oil in the external composition of the present invention is preferably at least 70% by weight of the weight of the composition as a whole minus the weight of the later mentioned powder component (in the case where a volatile component is formulated in the external composition, the weight of the powder component and the volatile component). By doing this, the transparency of the composition obtained becomes extremely high, and therefore, it becomes possible to more evenly cover skin roughness, no matter how large or how deep, to make it appear visually as if that roughness did not exist.

Further, to secure the transparency of the external composition of the present invention as a roughness correcting composition (specifically, a ΔL of at least 20: the value obtained by measurement using concealing rate test paper and a Minolta CM-1000 being the "L value" and the difference taken between the Hunter-Lab L value of a color obtained using the white portion of the concealing rate test paper as a background (white background) and the Hunter-Lab L value of a color obtained using the black portion as a background (black background) (measured at a thickness of the test composition of 2 mm) being made the "ΔL"), it is preferable to formula a powder component having a refractive index of 1.3 to 1.5 in a ratio of at least 90% by weight of the powder component as a whole. That is, if a powder component having a refractive index outside of this range is formulated in the external composition of the present invention over 10% by weight of the powder component as a whole, there is a strong tendency for the external composition of the present invention to become colored and the transparency is lost.

Even when the external composition of the present invention is a roughness correcting composition, however, it is possible to positively formulate in the above-mentioned dye or pigment etc. to color it and impart a desired color.

The roughness correcting composition of the present invention may be used, of course, in the field of cosmetics and may also be used in the field of medicine and the special makeup fields etc.

For example, the roughness correcting composition of the present invention of the form having a high transparency may be used in the field of cosmetics for applications of cosmetic foundations for concealing facial wrinkles. That is, by using the roughness correcting composition of the present invention of a form having a high transparency on the face in advance to correct roughness due to skin wrinkles and then using a usual makeup cosmetics on top of that, it is possible to use the composition for general purposes such as making the skin appear younger and use it for special purposes such as concealing scars.

Further, the roughness correcting composition of the present invention of a form having a high transparency may be directly used for makeup cosmetics to correct the roughness of the skin whereby the above general purposes and special purposes can be achieved.

The roughness correcting composition of the present invention can be used for "special purposes" such as covering and concealing scars, and therefore, can be used as a medicinal product for correcting surgical scars or burns.

Further, as explained above, the roughness correcting composition of the present invention having a form deliberately colored can, of course, be used for the above purposes. For example, when used for special makeup, it is advantageous in that it is easy to apply the desired formation on the skin.

(2) Case Where External Composition of Present Invention is "Makeup Composition"

A "makeup composition" means an external composition having as its object a more general makeup application that an external composition having as its main object the correction of relatively large roughness on the skin such as the above (1) to (5) etc. by the above "roughness correcting composition".

The makeup composition of the present invention is characterized in that it can naturally conceal, without an odd feeling, the large pores (for example, pores at scars of acne and other pimples; pores having a depth of about 150 μm) or small wrinkles which had been difficult to conceal naturally by existing makeup compositions (makeup cosmetics etc.)

To do this effectively, since it is necessary to positively adjust the thickness of coating of the composition on the skin (specifically, to set a coating thickness of about 20 μm), it is normally required that a composition have the property of enabling this and further the property of enabling natural concealment of the relatively large pores or small wrinkles on the skin to achieve a state where the pores or small wrinkles etc. cannot be discerned at all.

To suitably enable this adjustment of the coating thickness and natural concealment of the large pores or small wrinkles, it is possible to add the following elements in the makeup composition of the present invention.

That is, when the external composition of the present invention is a makeup composition, by formulating a volatile component as an essential component together with the low viscosity silicone oil so as to give a viscosity, together with the silicone-modified polysaccharide composition, of 1 to 10,000,000 mPa·s, preferably 1 to 100,000 mPa·s, at 25° C., it is possible to adjust the coating thickness of the external composition of the present invention on the skin (to be thinner than the roughness correcting composition (about 20 μm)) and possible to improve the adhesion to the skin and the ease of spreading on the skin.

By making the volatile component an essential component of the makeup composition of the present invention, it is possible to easily thinly coat the composition on the skin at the time of application, but after the application, the volatile component in the composition evaporates and a coating of a certain toughness can be quickly formed on the skin.

The total amount of the silicone-modified polysaccharide composition and the low viscosity silicone oil in the case where the external composition of the present invention is a makeup composition is preferably at least 60% by weight of the weight of the composition as a whole minus the weight of the powder component and the volatile component in order to enable the coating thickness of the composition on the skin to be adjusted to a desired thickness.

Further, in particular, when the external composition of the present invention is a makeup composition, it is preferable to formulate a powder component having a refractive index of 1.3 to 1.5 in a ratio of at least 20% by weight of the powder component as a whole depending upon the desired degree of coloring of the external composition. If the amount of formulation is less than 20% by weight of the powder component as a whole, it becomes difficult to maintain a natural finish even if concealing the large pores or small wrinkles by the external composition of the present invention.

Further, in the makeup composition of the present invention as well, it is possible to positively formulate the above mentioned dyes or pigments etc. for coloring to impart a desired color.

The makeup composition of the present invention can naturally conceal not only small pores etc., but also large pores and small wrinkles, and therefore can be used in the field of cosmetics, needless to say, and also the field of medicine etc.

The type of carrier when the external composition of the present invention is a makeup composition may be broadly selected from, for example, an oil type, an oil-in-water emulsion type, a water-in-oil emulsion type, a solid emulsion type, a solid powder type, a powder type, etc.

EXAMPLES

The present invention will now be explained in further detail with reference to Examples and Comparative Examples. However, the technical scope of the present invention is not limited in any way by these Examples etc. Note that in these Examples etc., the amounts of formulation (%), unless otherwise indicated, are % by weight based upon the entire system.

1. Examples of Case Where External Composition of Present Invention is Roughness Correcting Composition Examples 1 to 7 and Comparative Examples 1 to 3

According to the formulations shown in Table 1 and Table 2, the components were mixed homogeneously by a mortar to prepare the compositions and the performances of these as roughness correcting compositions were evaluated. The silicone-modified polysaccharide compound used was silicone-modified pullulan (substitution degree: about 1.7, molecular weight of pullulan: about 200,000).

The evaluations described in Table 1 and Table 2 were carried out according to the following methods:

(1) Roughness Smoothing Effect

A roughness correcting composition should be coated thicker than a conventional makeup etc. to smooth the skin roughness in order to effectively correct skin roughness.

In this test, the thickness of the standard coating layer was set to 5 mm and whether the test samples could be coated thickly or not and whether a roughness smoothing effect was recognized was studied.

Test Method

The test samples were coated on the cheeks by the fingers (the panel composed of 20 female panelists having either burns, scars, or deep wrinkles on their faces, the same for the following tests of actual use) to evaluate if they could be coated to a thickness of more than 5 mm (thickness of about earlobes).

Evaluation Criteria

Excellent (E): 15 to 20 out of 20 persons evaluated sample as being able to be coated to a thickness of at least 5 mm.

Good (G): 10 to 14 out of 20 persons evaluated sample as being able to be coated to a thickness of at least 5 mm.

Fair (F): 5 to 9 out of 20 persons evaluated sample as being able to be coated to a thickness of at least 5 mm.

Poor (P): 0 to 4 out of 20 persons evaluated sample as being able to be coated to a thickness of at least 5 mm.

(2) Adhesion to Skin with the Elapse of Time

A roughness correcting composition must maintain a state of adhesion to the skin after coating and not fall off by itself even after the elapse of time.

In this test, whether or not the test samples had this property was studied.

Test Method

The test samples were coated by the fingers on the cheeks and the adhesion to the skin after the elapse of two hours was visually evaluated.

Evaluation Criteria

Excellent (E): 15 to 20 out of 20 persons evaluated sample as adhering tightly to the skin.

Good (G): 10 to 14 out of 20 persons evaluated sample as adhering tightly to the skin.

Fair (F): 5 to 9 out of 20 persons evaluated sample as adhering tightly to the skin.

Poor (P): 0 to 4 out of 20 persons evaluated sample as adhering tightly to the skin.

(3) Lack of Running With the Elapse of Time

A roughness correcting composition preferably does not run due to its own weight after coating on the skin.

In the test, whether or not the test samples ran or not was studied.

Test Method

The test samples were coated by the fingers on the cheeks and whether or not they ran was visually evaluated.

Evaluation Criteria

Excellent (E): 15 to 20 out of 20 persons evaluated sample as not running.

Good (G): 10 to 14 out of 20 persons evaluated sample as not running.

Fair (F): 5 to 9 out of 20 persons evaluated sample as not running.

Poor (P): 0 to 4 out of 20 persons evaluated sample as not running.

(4) Ease of Removal from Skin

A roughness correcting composition preferably adheres to the skin after coating and can be easily removed.

In the test, whether the test samples can be easily removed after use was studied.

Test Method

The test samples were coated by the fingers on the cheeks and the ease of removal after the elapse of two hours was subjectively evaluated.

Evaluation Criteria

Excellent (E): 15 to 20 out of 20 persons evaluated sample as being easy to remove.

Good (G): 10 to 14 out of 20 persons evaluated sample as being easy to remove.

Fair (F): 5 to 9 out of 20 persons evaluated sample as being easy to remove.

Poor (P): 0 to 4 out of 20 persons evaluated sample as being easy to remove.

(5) Transparency

Under normal conditions, a roughness correcting composition preferably has a high transparency so long as enabling the appearance of use to be maintained natural.

In the test, the transparency after use of the test samples was studied.

Test Method

The test samples were coated by the fingers on the cheeks and the transparency was visually evaluated.

Evaluation Criteria

Excellent (E): 15 to 20 out of 20 persons evaluated sample as being transparent to semi-transparent.

Good (G): 10 to 14 out of 20 persons evaluated sample as being transparent to semi-transparent.

Fair (F): 5 to 9 out of 20 persons evaluated sample as being transparent to semi-transparent.

Poor (P): 0 to 4 out of 20 persons evaluated sample as being transparent to semi-transparent.

(6) Effect of Correction of Roughness

A roughness correcting composition is a composition designed to visually correct skin roughness such as keratoids, scars, or deep wrinkles so needless to say preferably it should appear that the skin roughness disappears as much as possible.

In the test, the effect of correction of roughness by the test samples was studied.

Test Method

The test samples were coated on the cheeks and whether or not it appeared to panelers that the roughness due to their keratoids, scars, or deep wrinkles disappeared was visually evaluated.

Evaluation Criteria

Excellent (E): 15 to 20 out of 20 persons evaluated roughness as appearing to disappear.

Good (G): 10 to 14 out of 20 persons evaluated roughness as appearing to disappear.

Fair (F): 5 to 9 out of 20 persons evaluated roughness as appearing to disappear.

Poor (P): 0 to 4 out of 20 persons evaluated roughness as appearing to disappear.

(7) Elasticity

A roughness correcting composition is as rich in elasticity as possible and has the same feeling as skin, but preferably gives a good feeling of the fit on the skin.

In the test, the elasticity of the test samples was studied.

Test Method

The test samples were coated by the fingers on the cheeks and the elasticity was subjectively evaluated.

Evaluation Criteria

Excellent (E): 15 to 20 out of 20 persons evaluated test sample as being elastic.

Good (G): 10 to 14 out of 20 persons evaluated test sample as being elastic.

Fair (F): 5 to 9 out of 20 persons evaluated test sample as being elastic.

Poor (P): 0 to 4 out of 20 persons evaluated test sample as being elastic.

(8) Ease of Application on Skin

A roughness correcting composition is preferably as easy to spread on the skin as possible to facilitate its use.

In the test, the ease of spreading of the test samples on the skin was studied.

Test Method

The test samples were coated by the fingers on the cheeks and the ease of spreading was subjectively evaluated.

Evaluation Criteria

Excellent (E): 15 to 20 out of 20 persons evaluated test sample as being easy to spread on the skin.

Good (G): 10 to 14 out of 20 persons evaluated test sample as being easy to spread on the skin.

Fair (F): 5 to 9 out of 20 persons evaluated test sample as being easy to spread on the skin.

Poor (P): 0 to 4 out of 20 persons evaluated test sample as being easy to spread on the skin.

(9) Last (the Adhesion of this Composition)

A roughness correcting composition must adhere to the skin for a long time after coating and maintain a pliable state, the portions in the deeper parts must not peel off and show up as white with the elapse of time, and the staying power must be superior.

In this test, whether the test sample had this property was studied.

Test Method

The test samples were coated by the fingers on the cheeks and the rising at deep portions after eight hours was visually evaluated.

Evaluation Criteria

Excellent (E): 15 to 20 out of 20 persons evaluated test sample as having no rising at deep portions.

Good (G): 10 to 14 out of 20 persons evaluated test sample as having no rising at deep portions.

Fair (F): 5 to 9 out of 20 persons evaluated test sample as having no rising at deep portions.

Poor (P): 0 to 4 out of 20 persons evaluated test sample as having no rising at deep portions.

(10) Toughness

A roughness correcting composition must be tough on the skin and not break up due to skin movement.

In this test, whether the test samples had this property was studied.

Test Method

The test samples were coated by the fingers on the cheeks and the toughness was visually evaluated.

Evaluation Criteria

Excellent (E): 15 to 20 out of 20 persons evaluated test sample as being tough.

Good (G): 10 to 14 out of 20 persons evaluated test sample as being tough.

Fair (F): 5 to 9 out of 20 persons evaluated test sample as being tough.

Poor (P): 0 to 4 out of 20 persons evaluated test sample as being tough.

TABLE 1

| Components | Ex. 1 | Ex. 2 | Ex. 3 | Ex. 4 | Ex. 5 | Ex. 6 | Ex. 7 |
|---|---|---|---|---|---|---|---|
| Dimethyl polysiloxane (6 mPa · s/25° C.) | 50.0 | 15.0 | 45.0 | 55.0 | 52.5 | 28.0 | 55.0 |
| Dimethyl polysiloxane (100,000 mPa · s/25° C.) | — | — | — | — | — | — | — |
| Dimethyl polysiloxane (15,000,000 mPa · s/25° C.) | — | — | — | — | — | — | — |
| Amorphous silica (0.016 μm) (refractive index 1.46) | — | — | — | 15.0 | 15.0 | — | 15.0 |
| Spherical silicone rubber powder (5 μm, rubber hardness 30) (refractive index 1.39) | 30.0 | — | — | — | — | — | 15.0 |
| Spherical silicone resin powder (5 μm) (refractive index 1.39) | — | 65.0 | — | — | — | — | — |
| Spherical silicone resin coated rubber powder (5 μm, rubber hardness 30) (refractive index 1.39) | — | — | 35.0 | 15.0 | — | — | — |
| Spherical silicone resin coated rubber powder (8 μm, rubber hardness 13) (refractive index 1.39) | — | — | — | — | 12.5 | — | — |
| Spherical silicone resin coated rubber powder (5 μm, rubber hardness 79) (refractive index 1.39) | — | — | — | — | — | 52.0 | — |
| Silicone-modified pullulan | 20.0 | 20.0 | 20.0 | 15.0 | 20.0 | 20.0 | 15.0 |
| Results of evaluation | | | | | | | |
| (1) Roughness smoothing effect | E | E | E | E | E | E | E |
| (2) Adhesion to skin (over time) | G | E | G | E | E | E | E |
| (3) Lack of running over time | E | E | E | E | E | E | E |
| (4) Ease of removal from skin | G | G | G | G | G | G | G |

TABLE 1-continued

| Components | | Ex. 1 | Ex. 2 | Ex. 3 | Ex. 4 | Ex. 5 | Ex. 6 | Ex. 7 |
|---|---|---|---|---|---|---|---|---|
| (5) | Transparency | E | E | E | E | E | E | E |
| (6) | Roughness correcting effect (making it appear there is no roughness) | E | E | E | E | E | E | E |
| (7) | Elasticity | E | G | E | E | E | G | E |
| (8) | Ease of spreading on skin | E | G | G | G | E | G | E |
| (9) | Last (the adhesion of this composition) | G | E | G | E | E | E | E |
| (10) | Toughness | E | G | G | G | E | G | E |

TABLE 2

| | Comparative Examples | | |
|---|---|---|---|
| | 1 | 2 | 3 |
| Components | | | |
| Dimethyl polysiloxane (6 mPa · s/25° C.) | 10.0 | 12.0 | 5.0 |
| Dimethyl polysiloxane (100,000 mPa · s/25° C.) | 20.0 | 20.0 | 20.0 |
| Dimethyl polysiloxane (15,000,000 mPa · s/25° C.) | 3.0 | 3.0 | 3.0 |
| Amorphous silica (0.016 μm) | 10.0 | — | 10.0 |
| Spherical silicone rubber powder (5 μm, rubber hardness 30) | 47.0 | — | — |
| Spherical silicone resin powder (5 μm) | — | 65.0 | — |
| Spherical silicone resin coated rubber powder (5 μm, rubber hardness 30) | — | — | 52.0 |
| Spherical silicone resin coated rubber powder (8 μm, rubber hardness 13) | — | — | — |
| Spherical silicone resin coated rubber powder (5 μm, rubber hardness 79) | — | — | — |
| Silicone-modified pullulan | — | — | — |
| Results of evaluation | | | |
| (1) Roughness smoothing effect | G | G | G |
| (2) Adhesion to skin (over time) | F | G | F |
| (3) Lack of running over time | E | E | E |
| (4) Ease of removal from skin | G | G | G |
| (5) Transparency | E | E | E |
| (6) Roughness correcting effect (making it appear there is no roughness) | G | G | G |
| (7) Elasticity | F | P | F |
| (8) Ease of spreading on skin | G | P | G |
| (9) Last (the adhesion of this composition) | P | F | P |
| (10) Toughness | P | P | P |

As shown in Table 1 and Table 2, the external skin compositions of the present invention of Examples 1 to 7 were found to have superior properties as roughness correcting compositions. The external skin compositions of the present invention were superior in last (the adhesion of this composition) and toughness compared with the external skin compositions of Comparative Examples 1 to 3 and had more preferable properties as roughness correcting compositions overall.

2. Examples of Case Where External Composition of Present Invention is Makeup Composition Examples 8 to 16 and Comparative Examples 4 to 8

The components according to the formulations in Table 3 (type of carrier: oil composition, Examples 8 to 12 and Comparative Example 4), Table 4 (type of carrier: W/o type emulsion composition, Example 13 and Comparative Example 5), Table 5 (type of carrier: W/o type emulsion composition, Example 14 and Comparative Example 6), Table 6 (O/W type emulsion composition, Example 15 and Comparative Example 7), and Table 7 (O/W type solid emulsion composition, Example 16 and Comparative Example 8) were used to produce compositions by ordinary methods in accordance with the forms concerned and the performances as makeup compositions were evaluated. The silicone-modified polysaccharide composition used was silicone-modified pullulan (substitution degree: approximately 1.7, molecular weight of pullulan component: approximately 200,000).

The evaluations in Table 3 to Table 7 were performed according to the following methods:

(1) Pore and Small Wrinkle Correction Test

A makeup composition of the present invention should correct large pores in the skin or small wrinkles giving a natural look making it appear as if there were no large pores or small wrinkles from the start.

In this test, the thickness of the standard coating layer was set to about 20 μm and it was studied if it was possible to smoothly coat the test samples and if an effect of correction of the pores and small wrinkles was observed right after coating.

Test Method

The test samples were coated on the cheek by the fingers in the same way as coating an ordinary foundation (the panel was composed of 20 female panelists suffering from acne scars forming noteworthy pores or so-called "crow's feet" appearing at the sides of the eyes when smiling) and whether this corrected the pores and small wrinkles (crow's feet) to make it appear as if the pores or small wrinkles did not exist from the start was evaluated.

Evaluation Criteria

Excellent (E): 15 to 20 out of 20 persons evaluated pores or small wrinkles as being corrected to appear as if they originally did not exist.

Good (G): 10 to 14 out of 20 persons evaluated pores or small wrinkles as being corrected to appear as if they originally did not exist.

Fair (F): 5 to 9 out of 20 persons evaluated pores or small wrinkles as being corrected to appear as if they originally did not exist.

Poor (P): 0 to 4 out of 20 persons evaluated pores or small wrinkles as being corrected to appear as if they originally did not exist.

(2) Test of "Naturalness of Finish"

At the same time as the above pore and small wrinkle correction test, the "naturalness of the finish" was subjectively evaluated.

Evaluation Criteria

Excellent (E): 15 to 20 out of 20 persons evaluated finish as being natural.

Good (G): 10 to 14 out of 20 persons evaluated finish as being natural.

Fair (F): 5 to 9 out of 20 persons evaluated finish as being natural.

Poor (P): 0 to 4 out of 20 persons evaluated finish as being natural.

(3) Stability Test with the Elapse of Time

The test samples were allowed to stand at room temperature for three years to study if there were any changes (for example, phase separation) during that time.

TABLE 3

|  | Ex. 8 | Ex. 9 | Ex. 10 | Ex. 11 | Ex. 12 | Comp. Ex. 4 |
|---|---|---|---|---|---|---|
| Spherical silicone rubber powder (5 μm, rubber hardness 30) | 6.4 | 4.6 | 4.6 | 4.6 | 4.6 | 4.6 |
| Amorphous silica (0.016 μm) | 4.6 | 6.4 | 6.4 | 6.4 | 6.4 | 6.4 |
| Hydrophobic titanium oxide (refractive index 2.4) | 13.0 | 13.0 | 13.0 | 13.0 | 13.0 | 13.0 |
| Hydrophobic iron oxide (refractive index 2.1) | 3.0 | 3.0 | 3.0 | 3.0 | 3.0 | 3.0 |
| Silicone-modified pullulan | 6.0 | 6.0 | 6.0 | 6.0 | 6.0 | — |
| Dimethyl polysiloxane (5000 mPa · s/25° C.) | — | — | — | — | — | 6.0 |
| Dimethyl polysiloxane (6 mPa · s/25° C.) | 27.0 | 27.0 | 27.0 | 27.0 | 27.0 | 27.0 |
| Methylphenyl polysiloxane | — | — | — | 5.0 | — | — |
| Liquid paraffin | — | — | — | — | 5.0 | — |
| Isostearic acid | — | — | — | 1.0 | 1.0 | — |
| Octylmethoxy cinnamate | — | — | — | — | 5.0 | — |
| Decamethyl cyclopentasiloxane | 40.0 | 40.0 | 35.0 | 34.0 | 29.0 | 40.0 |
| Ethanol | — | — | 5.0 | — | — | — |
| Pore correcting effect | G | E | E | E | E | P |
| Naturalness of finish | E | E | E | E | E | E |

TABLE 4

|  | Ex. 13 | Comp. Ex. 5 |
|---|---|---|
| Spherical silicone rubber powder (5 μm, refractive index 1.39, rubber hardness 30) | 4.0 | 4.0 |
| Amorphous silica (0.016 μm) | 5.0 | 5.0 |
| Hydrophobic titanium oxide (refractive index 2.4) | 13.0 | 13.0 |
| Hydrophobic iron oxide (refractive index 2.1) | 3.0 | 3.0 |
| Silicone-modified pullulan | 6.0 | — |
| Dimethyl polysiloxane (5000 mPa · s/25° C.) | — | 6.0 |
| Dimethyl polysiloxane (6 mPa · s/25° C.) | 16.0 | 16.0 |
| Methylphenyl polysiloxane | 5.0 | 5.0 |
| Organo-modified dimethyl polysiloxane | 3.0 | 3.0 |
| Chlorinated distearyl dimethyl ammonium | 0.2 | 0.2 |
| Palmitic acid | 0.4 | 0.4 |
| Isostearic acid | 1.0 | 1.0 |
| Paraffin wax | 5.0 | 5.0 |
| 1,3-butylene glycol | 5.0 | 5.0 |
| Methylparaben | 0.2 | 0.2 |
| Decamethyl cyclopentasiloxane | 16.2 | 16.2 |
| Water | 17.0 | 17.0 |
| Antioxidant | q.s. | q.s. |
| Pore correcting effect | G | F |
| Naturalness of finish | E | E |

TABLE 5

|  | Ex. 14 | Comp. Ex. 6 |
|---|---|---|
| Spherical silicone rubber powder (5 μm, refractive index 1.39, rubber hardness 30) | 4.0 | 4.0 |
| Amorphous silica (0.016 μm) | 5.0 | 5.0 |
| Hydrophobic titanium oxide (refractive index 2.4) | 13.0 | 13.0 |
| Hydrophobic iron oxide (refractive index 2.1) | 3.0 | 3.0 |
| Silicone-modified pullulan | 6.0 | — |
| Dimethyl polysiloxane (5000 mPa · s/25° C.) | — | 6.0 |
| Dimethyl polysiloxane (6 mPa · s/25° C.) | 16.0 | 16.0 |
| Methylphenyl polysiloxane | 5.0 | 5.0 |
| Organo-modified dimethyl polysiloxane | 2.5 | 2.5 |
| Isostearic acid | 1.0 | 1.0 |
| 1,3-butylene glycol | 5.0 | 5.0 |
| Methylparaben | 0.2 | 0.2 |
| Decamethyl cyclopentasiloxane | 19.3 | 19.3 |
| Water | 20.0 | 20.0 |
| Antioxidant | q.s | q.s |
| Pore correcting effect | G | F |
| Naturalness of finish | E | E |

TABLE 6

|  | Ex. 15 | Comp. Ex. 7 |
|---|---|---|
| Spherical silicone rubber powder (5 μm, refractive index 1.39, rubber hardness 30) | 3.0 | 3.0 |
| Amorphous silica (0.016 μm) | 4.0 | 4.0 |
| Hydrophobic titanium oxide (refractive index 2.4) | 6.5 | 6.5 |
| Hydrophobic iron oxide (refractive index 2.1) | 1.5 | 1.5 |
| Silicone-modified pullulan | 6.0 | — |
| Dimethyl polysiloxane (5000 mPa · s/25° C.) | — | 6.0 |
| Dimethyl polysiloxane (6 mPa · s/25° C.) | 5.0 | 5.0 |
| Methylphenyl polysiloxane | 5.0 | 5.0 |
| 1,3-butylene glycol | 0.5 | 0.5 |
| Stearic acid | 1.0 | 1.0 |
| Palmitic acid | 1.0 | 1.0 |
| Triethanolamine | 0.5 | 0.5 |
| Glyceryl monostearate | 0.5 | 0.5 |
| Bentonite | 1.0 | 1.0 |
| Methylparaben | 0.3 | 0.3 |
| Decamethyl cyclopentasiloxane | 0.3 | 19.3 |
| Water | 45.7 | 20.0 |
| Antioxidant | q.s | q.s |
| Pore correcting effect | G | F |
| Naturalness of finish | E | E |

TABLE 7

|  | Ex. 16 | Comp. Ex. 8 |
|---|---|---|
| Spherical silicone rubber powder (5 μm, refractive index 1.39, rubber hardness 30) | 4.6 | 4.6 |
| Amorphous silica (0.016 μm) (refractive index 1.46) | 6.4 | 6.4 |
| Titanium oxide (refractive index 2.4) | 6.5 | 6.5 |
| Iron oxide (refractive index 2.1) | 1.5 | 1.5 |
| Silicone-modified pullulan | 4.0 | — |
| Dimethyl polysiloxane (5000 mPa · s/25° C.) | — | 4.0 |
| Dimethyl polysiloxane (6 mPa · s/25° C.) | 17.8 | 17.8 |
| Methylphenyl polysiloxane | 5.0 | 5.0 |

TABLE 7-continued

| | Ex. 16 | Comp. Ex. 8 |
|---|---|---|
| 1,3-butylene glycol | 4.0 | 4.0 |
| Isostearic acid | 1.0 | 1.0 |
| Imidazolium betaine | 1.0 | 1.0 |
| Sodium carboxymethylcellulose | 0.5 | 0.5 |
| Xanthane gum | 0.5 | 0.5 |
| Bentonite | 1.0 | 1.0 |
| Methylparaben | 0.2 | 0.2 |
| Microcrystalline wax | 1.0 | 1.0 |
| Candelilla wax | 3.0 | 3.0 |
| Decamethyl cyclopentasiloxane | 2.0 | 2.0 |
| Water | 40.0 | 40.0 |
| Antioxidant | q.s | q.s |
| Pore correcting effect | G | F |
| Naturalness of finish | E | E |

From Table 3 to Table 7, it became clear that the makeup composition of the present invention, regardless of the specific form, can correct large pores or small wrinkles while maintaining a natural look.

Further, the test samples of the Examples of the invention remained stable without phase separation etc. in a three-year stability test.

INDUSTRIAL APPLICABILITY

As explained above, according to the present invention, there is provided an external composition able to cover and smooth the roughness formed due to various reasons on the skin and visually correct roughness to make it appear as if it did not exist.

What is claimed is:

1. An external composition, which is applied to skin and comprises
   (a) a component for correcting skin roughness consisting essentially of a silicone-modified polysaccharide compound;
   (b) a silicone oil having a viscosity of 1 to 1000 mPa's at 25° C.; and
   (c) at least one powder component having a refractive index of 1.3 to 1.5 and wherein said powder component comprises (i) at least one powder selected from the group consisting of silicone resin powder, silicone rubber powder, and silicone resin-coated rubber powder and (ii) an amorphous silicone dioxide powder in an amount of 10–90% by weight, based upon the total amount of the powder component;
   (d) a volatile component selected from the group consisting of a volatile silicone oil, water and a lower alcohol having 1 to 4 carbon atoms.

2. An external composition as claimed in claim 1, wherein the silicone-modified polysaccharide compound is silicone-modified pullulan.

3. An external composition as claimed in claim 1, wherein said powder component is a rubber powder having an average rubber hardness of less than 50.

4. An external composition as claimed in claim 1, wherein the powder component contains at least two powder particles having different shapes selected from the group consisting of spherical, plate-shaped and amorphous shapes.

5. An external composition as claimed in claim 1, wherein the total amount of the silicone-modified polysaccharide corn pound and the silicone-oil is at least 70% by weight, based upon the weight obtained by subtracting the weight of the powder component, or the total weight of the powder and a volatile component when the volatile component is present in the external composition, from the total weight of the external composition.

6. An external composition as claimed in claim 1 wherein at least 90% by weight of the total powder component is a powder component having a refractive index of 1.3 to 1.5.

7. An external composition as claimed in claim 1 or 8, wherein the external composition is a roughness correcting composition.

8. An external composition as claimed in claim 1, wherein the total amount of the silicone-modified polysaccharide compound and the silicone oil is at least 60% by weight, based upon the weight obtained by subtracting the weight of the powder component and the volatile component from the total amount of the external composition.

9. An external composition as claimed in claim 1, wherein at least 20% by weight of the total powder component is a powder component having a refractive index of 1.3 to 1.5.

10. An external composition as claimed in claim 8, wherein the external composition is a makeup composition.

11. An external composition as claimed in claim 1, wherein the component for correcting skin roughness is a silicone-modified polysaccharide compound.

12. An external composition as claimed in claim 11, wherein the silicone-modified polysaccharide composition is silicone-modified pullulan.

13. An external composition as claimed in claim 3, wherein the silicone-modified polysaccharide compound is silicone-modified pullulan.

14. An external composition as claimed in claim 1, wherein the lower alcohol is selected from the group consisting of methanol and ethanol.

15. An external composition as claimed in claim 1, wherein the lower alcohol is ethanol.

16. A method for correcting akin roughness comprising applying to a person in need of such correction, the external composition according to claim 1.

17. A method as claimed in claim 16, wherein the silicone-modified polysaccharide compound is silicone-modified pullulan.

18. An external composition as claimed in claim 1, wherein said powder component comprises at least one powder selected from the group consisting of silicone rubber powder and silicone resin-coated rubber powder.

* * * * *

UNITED STATES PATENT AND TRADEMARK OFFICE
CERTIFICATE OF CORRECTION

PATENT NO. : 6,703,027 B2
DATED : March 9, 2004
INVENTOR(S) : Mari Kurosawa and Hiroshi Fukui It is certified that error appears in the above-identified patent and that said Letters Patent is hereby corrected as shown below:

<u>Title page,</u>
Item [54], Title, change "COMPOSITION FOR EXTERNAL USE" to
-- EXTERNAL COMPOSITION --.

Signed and Sealed this

Eighteenth Day of May, 2004

JON W. DUDAS
*Acting Director of the United States Patent and Trademark Office*